(12) United States Patent
Zhang (10) Patent No.: US 10,064,560 B2
(45) Date of Patent: Sep. 4, 2018

(54) SYSTEM FOR CARDIAC PATHOLOGY DETECTION AND CHARACTERIZATION (75) Inventor: Hongxuan Zhang, Palatine, IL (US)

(73) Assignee: Siemens Healthcare GmbH, Erlangen (DE)

(*) Notice: Subject to any disclaimer, the term of this patent is extended or adjusted under 35 U.S.C. 154(b) by 1770 days.

(21) Appl. No.: 12/754,644

(22) Filed: Apr. 6, 2010

(65) Prior Publication Data
US 2010/0312125 A1 Dec. 9, 2010

Related U.S. Application Data (60) Provisional application No. 61/184,352, filed on Jun. 5, 2009.

(51) Int. Cl.
A61B 5/02 (2006.01)
A61B 5/021 (2006.01)
A61B 5/0215 (2006.01)
A61B 5/00 (2006.01)

(52) U.S. Cl.
CPC .......... *A61B 5/021* (2013.01); *A61B 5/02028* (2013.01); *A61B 5/02116* (2013.01); *A61B 5/02158* (2013.01); *A61B 5/7257* (2013.01)

(58) Field of Classification Search
CPC ..... A61B 5/02154; A61B 5/021; A61B 5/441; A61B 5/0205; A61B 5/0215; A61B 5/02152; A61B 5/02216; A61B 5/022; A61B 5/02208; A61B 5/02225; A61B 5/023; A61B 5/0235; A61B 5/02233; A61B 5/024; A61B 5/02438; A61B 5/026; A61B 5/028; A61B 5/0535; A61B 5/0452
USPC .................................. 600/480–507
See application file for complete search history.

(56) References Cited

U.S. PATENT DOCUMENTS

| | | | |
|---|---|---|---|
| 4,356,827 A | 11/1982 | Uemura et al. | |
| 4,432,374 A | 2/1984 | Osanai | |
| 4,649,929 A | 3/1987 | Weaver et al. | |
| 5,105,816 A | 4/1992 | Shimura et al. | |
| 5,265,615 A | 11/1993 | Frank et al. | |

(Continued)

OTHER PUBLICATIONS

Lu, Zhenwei et al., "Continuous cardiac output monitoring in humans by invasive and noninvasive peripheral blood pressure waveform analysis", J Appl Physiol, vol. 101, pp. 598-608, 2006.

(Continued)

*Primary Examiner* — Navin Natnithithadha
*Assistant Examiner* — Andrey Shostak (57) ABSTRACT A system for heart performance characterization and abnormality detection includes an interface for receiving digitized electrical signals representing blood pressure waveforms over one or more heart beat cycles. The digitized electrical signals comprise, a first digital data sequence representing normal blood pressure of a patient, a second digital data sequence representing random blood pressure of a normal patient and a third digital data sequence representing a potentially abnormal blood pressure of a patient. A complexity processor calculates first, second and third complexity indices for the corresponding first, second and third digital data sequences respectively. A correlation processor uses the calculated first, second and third complexity indices to calculate one or more measures indicating deviation of the potentially abnormal blood pressure of the patient from a normal value.

13 Claims, 8 Drawing Sheets

(56) References Cited

U.S. PATENT DOCUMENTS

| | | | |
|---|---|---|---|
| 5,297,556 A * | 3/1994 | Shankar | 600/481 |
| 5,390,679 A | 2/1995 | Martin | |
| 5,392,781 A | 2/1995 | Phillipps et al. | |
| 5,772,600 A | 6/1998 | Kahn et al. | |
| 5,797,850 A | 8/1998 | Archibald et al. | |
| 5,881,130 A | 3/1999 | Zhang | |
| 5,913,826 A | 6/1999 | Blank | |
| 5,931,790 A | 8/1999 | Peel, III | |
| 6,007,491 A | 12/1999 | Ling et al. | |
| 6,045,510 A * | 4/2000 | Ogura et al. | 600/485 |
| 6,120,441 A | 9/2000 | Griebel | |
| 6,454,721 B1 | 9/2002 | deBoisblanc et al. | |
| 6,506,163 B1 | 1/2003 | Farrell et al. | |
| 6,736,782 B2 | 5/2004 | Pfeiffer et al. | |
| 6,746,403 B2 | 6/2004 | Kolluri et al. | |
| 6,878,116 B2 | 4/2005 | Su | |
| 6,923,769 B2 | 8/2005 | Nishii et al. | |
| 7,043,293 B1 | 5/2006 | Baura | |
| 7,160,250 B2 | 1/2007 | Lemaire | |
| 7,228,171 B2 | 6/2007 | Lesser et al. | |
| 7,308,319 B2 | 12/2007 | Lovett et al. | |
| 7,364,550 B1 | 4/2008 | Turcott | |
| 7,374,539 B2 | 5/2008 | Fernando et al. | |
| 7,458,937 B2 | 12/2008 | Elliott | |
| 7,479,111 B2 | 1/2009 | Zhang et al. | |
| 7,559,898 B2 * | 7/2009 | Eide | 600/485 |
| 2003/0212316 A1 * | 11/2003 | Leiden et al. | 600/323 |
| 2004/0030261 A1 | 2/2004 | Rantala | |
| 2005/0096557 A1 | 5/2005 | Vosburgh et al. | |
| 2007/0260285 A1 * | 11/2007 | Libbus et al. | 607/9 |

OTHER PUBLICATIONS

McKinley, Paula et al., "Deriving heart period variability from blood pressure waveforms", J Appl Physiol, vol. 95, pp. 1431-1438, 2003.

Thakor, N.V. et al., "Nonlinear changes in brain's response in the event of injury as detected by adaptive coherence estimation of evoked potentials", Biomedical Engineering, IEEE Transactions on; vol. 42, Issue 1, Jan. 1995 pp. 42-51.

* cited by examiner

SYSTEM FOR CARDIAC PATHOLOGY DETECTION AND CHARACTERIZATION

This is a non-provisional application of provisional application Ser. No. 61/184,352 filed Jun. 5, 2009, by H. Zhang.

FIELD OF THE INVENTION

This invention concerns a system for heart performance characterization and abnormality detection involving calculating measures indicating deviation of potentially abnormal blood pressure of a patient from a normal value.

BACKGROUND OF THE INVENTION

Invasive and non-invasive blood pressure analysis is used for heart and cardiac circulation monitoring and function evaluation. Usually blood pressures measurement at different sites (such as left atrial, right atrial) and cardiac output calculation are utilized to diagnose and characterize cardiac function and patient health status. Known clinical methods for blood pressure analysis do not fully capture patient health information from monitored pressure. Some known systems use a blood velocity waveform and calculate magnitude-squared coherence (MSC) for analysis of cardiovascular diseases (such as material hypertension during pregnancy) but fail to provide qualitative and quantitative analysis and evaluation of a blood pressure waveform.

The cardiovascular system comprises a pump (the heart), a carrier fluid (blood), a distribution system (arteries), an exchange system (capillary network), and a collecting system (venous system). Blood pressure is the driving force that propels blood along the distribution network. Hemodynamic signal (especially blood pressure waveform and data) analysis is used for characterization of cardiac pathology and disorders. Accurate hemodynamic signal (invasive and non-invasive blood pressure signal) measurement and (True positive and false negative rate) evaluation are desirable to monitor patient health status. Known methods of using blood pressure signals typically focus on stroke volume and cardiac output calculation. Further known hemodynamic signal and pressure waveform analysis is mostly used for qualitative diagnosis and analysis of the cardiac functions, such as low perfusion and pressure amplitude variation. Some known methods use pressure signal integration analysis and calculation (e.g. based on ventricular end-diastolic volume (EDV) and end-systolic volume (ESV)) for cardiac function evaluation, such as SV (stroke volume) and cardiac output. But these methods fail to comprehensively and effectively use the hemodynamic signals and waveform characteristics.

Usually changes and distortions due to cardiac malfunctions and arrhythmia affect the cardiac tissue earlier than electrophysiological characteristics. Known clinical systems fail to comprehensively detect early changes and deviations of such malfunctions (which are usually small), such as blood pressure magnitude and ECG signal distortions. Electrophysiological signals (ECG, ICEG) and hemodynamic signals capture different information concerning cardiac diseases and heart malfunctions. Known systems use different methods to interpret electrophysiological signals, such as RR wave detection, ST elevation, PQRST morphology deviation. However, electrophysiological signals are often corrupted by electrical noise and bio-artifacts, such as power line noise and patient movement. Hemodynamic signals (such as blood pressure) may provide better noise immunity and cardiac function analysis stability. A system according to invention principles addresses the identified deficiencies and related problems and provides qualitative and quantitative analysis of a blood pressure waveform.

SUMMARY OF THE INVENTION

A system improves sensitivity and reliability of blood pressure interpretation by analyzing and characterizing blood pressure waveform data using hemodynamic waveform signal coherence, for example, to identify and characterize cardiac disorders. A system for heart performance characterization and abnormality detection includes an interface for receiving digitized electrical signals representing blood pressure waveforms over one or more heart beat cycles. The digitized electrical signals comprise, a first digital data sequence representing normal blood pressure of a patient, a second digital data sequence representing random blood pressure of a normal patient and a third digital data sequence representing a potentially abnormal blood pressure of a patient. A complexity processor calculates first, second and third complexity indices for the corresponding first, second and third digital data sequences respectively. A correlation processor uses the calculated first, second and third complexity indices to calculate one or more measures indicating deviation of the potentially abnormal blood pressure of the patient from a normal value.

DETAILED DESCRIPTION OF THE INVENTION

A system improves sensitivity and reliability of blood pressure signal interpretation by analyzing and characterizing blood pressure waveform data using hemodynamic waveform signal coherence, for example. The system identifies nonlinear signal and waveform changes due to pathologies or medical events by accurate interpretation of an invasive and non-invasive blood pressure waveform signal and data. The system identifies cardiac disorders, categorizes cardiac arrhythmia, characterizes pathological severity, predicts life-threatening events, and evaluates drug delivery effects.

The system provides patient health information from pressure waveform monitoring, including waveform morphology variation, identified waveform components, amplitude and frequency variability, blood pressure patterns and blood pressure nonlinearity correlation with cardiac arrhythmias. The system combines hemodynamic signal (blood pressure and waveform morphology) analysis and electrophysiological signal analysis to improve clinical signal interpretation for use by healthcare workers. The system analyzes a blood pressure waveform using windowed coherence, complexity coherence, multi-bandwidth and multi-channel coherence for cardiac status characterization, for example. The system improves sensitivity and reliability of analysis and interpretation of patient cardiac status and health and particularly nonlinear changes in hemodynamic signals due to the arrhythmia or cardiac events and provides predictive indication of different types of arrhythmias and cardiac malfunction location, such as AF (atrial fibrillation) and MI (myocardial ischemia).

In one embodiment, different kinds of signals, including electrophysiological signals, oximetric signals (such as SPO2), are used in combination for precise synchronization of hemodynamic signals to improve sensitivity and accuracy of signal analysis. Multi-channel signal pattern and mode analysis is performed (including single-channel coherence, cross-channel coherence) of hemodynamic signals. The system in a further embodiment uses an artificial neural network (ANN) for analysis but in other embodiments may use a fuzzy system or expert system, for example. The system maps hemodynamic signal data of a heart and circulation system (including tissue, function, activities) to medical conditions based on multi-channel blood pressure mode and pattern analysis using external and internal pressures derived from different locations in patient anatomy. The system may be implemented in software or firmware or a combination of both in medical devices in ICD (implantable cardioverter-defibrillator) equipment using blood pressure pattern analysis.

Hemodynamic signals, such as invasive and non-invasive blood pressure (IBP and NIBP) waveforms and related waveform calculations (such as dP/dt), are used to interpret, evaluate and quantitatively characterize heart function, arrhythmias, and patient health status. The system advantageously employs a wider range of properties and characteristics of hemodynamic signals and waveforms for cardiac function and rhythm diagnosis, including waveform morphology variation and spectrum coherence. The system advantageously determines coherence parameters of a hemodynamic signal and pressure waveform at multiple cardiac sites and maps the parameters to heart conditions using predetermined mapping information.

Figure 1:
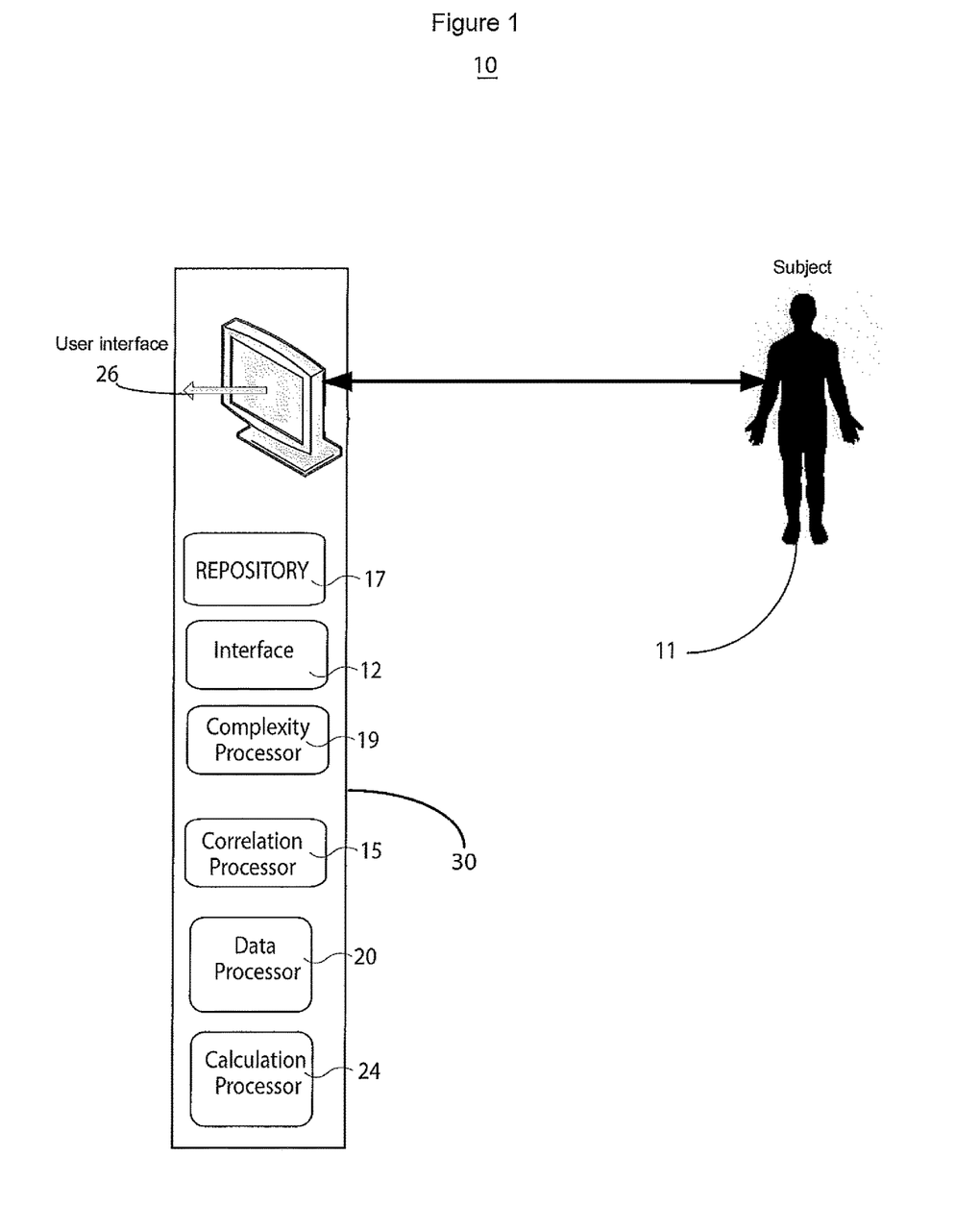
FIG. 1 shows a system for heart performance characterization and abnormality detection, according to invention principles.

FIG. 1 shows system 10 for heart performance characterization and abnormality detection. Magnitude based pressure waveform analysis may not be able to accurately characterize nonlinear changes in a blood pressure representative signal waveform (indicating morphology) or frequency component distortion of blood pressure signals. System 10 uses coherence analysis (which is based on complexity calculation and on spectrum distribution) for blood pressure pattern analysis and waveform feature quantification. The system determines coherence by extracting a linear association by comparing a baseline blood pressure signal and an on-going blood pressure waveform. Due to cardiac events, such as arrhythmias, this linear association varies because of signal component changes, such as frequency component changes and such changes are indicated by complexity calculations. System 10 uses cardiac hemodynamic signal analyses of invasive (intra-cardiac) blood pressure and non-invasive blood pressure to qualitatively and quantitatively test and evaluate heart activity and abnormality, such as tissue and cardiac functions. A system 10 complexity calculation characterizes and differentiates cardiac pathologies and differentiates between severity of cardiac signals having the same rhythm. A detailed illustration of calculation of complexity is shown in the appendix.

System 10 comprises at least one computer system, workstation, server or other processing device 30 including interface 12, repository 17, complexity processor 19, correlation processor 15, data processor 20, calculation processor 24 and a user interface 26. Interface 12 receives digitized electrical signals representing blood pressure waveforms over one or more heart beat cycles. The digitized electrical signals comprise, a first digital data sequence representing normal blood pressure of a patient, a second digital data sequence representing random blood pressure of a normal patient and a third digital data sequence representing a potentially abnormal blood pressure of patient 11. Complexity processor 19 calculates first, second and third complexity indices for the corresponding first, second and third digital data sequences respectively. Correlation processor 15 uses the calculated first, second and third complexity indices to calculate one or more measures indicating deviation of the potentially abnormal blood pressure of the patient from a normal value. Calculation processor 24 determines measures derived from Fourier transform values of components of a received digitized electrical signal.

Figure 2:
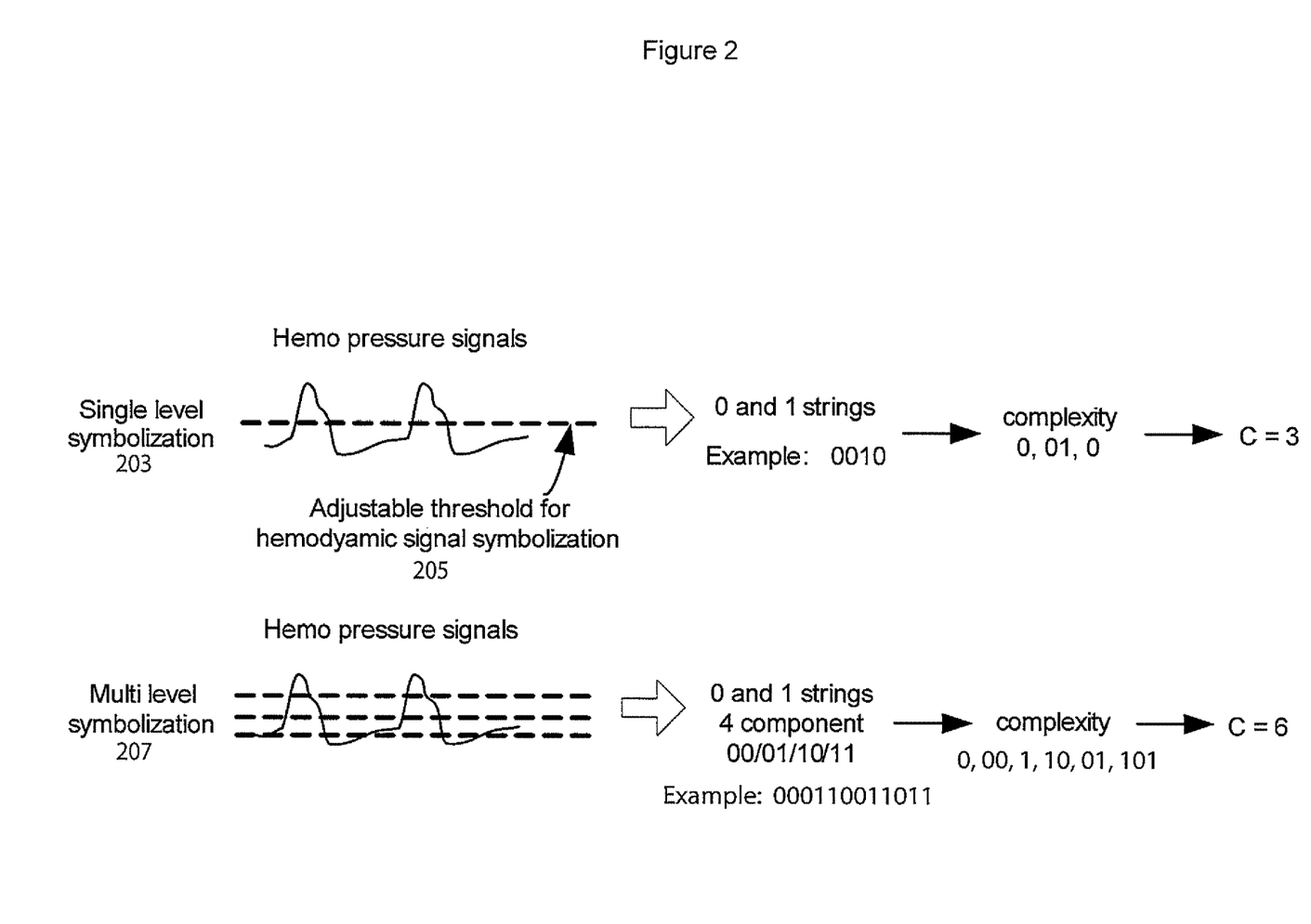
FIG. 2 illustrates complexity calculation for a hemodynamic pressure signal based on adjustable symbolization, according to invention principles.

FIG. 2 illustrates complexity calculation performed by complexity processor 19 (FIG. 1) using hemodynamic pressure signal based adjustable symbolization. Different methods may be used for symbolic complexity index calculation and computation. In one embodiment, complexity processor 19 adaptively selects between different types of symbolic complexity index calculation in response to data indicating clinical application and accuracy or resolution requirements, to capture smaller signal changes in a signal, for example. A user is also able to select a particular hemodynamic signal calculation based on a desired clinical application. A first type of symbolic complexity index calculation comprises single level symbolization calculation 203 employing adaptable threshold 205 for symbolization of a blood pressure signal into binary (0 and 1) strings having a complexity value C of 3. A second type of symbolic complexity index calculation comprises multi-level symbolization calculation 207 employing multiple adaptable thresholds for symbolization of a blood pressure signal into binary (0 and 1) strings having four components and a complexity value C of 6.

Figure 3:
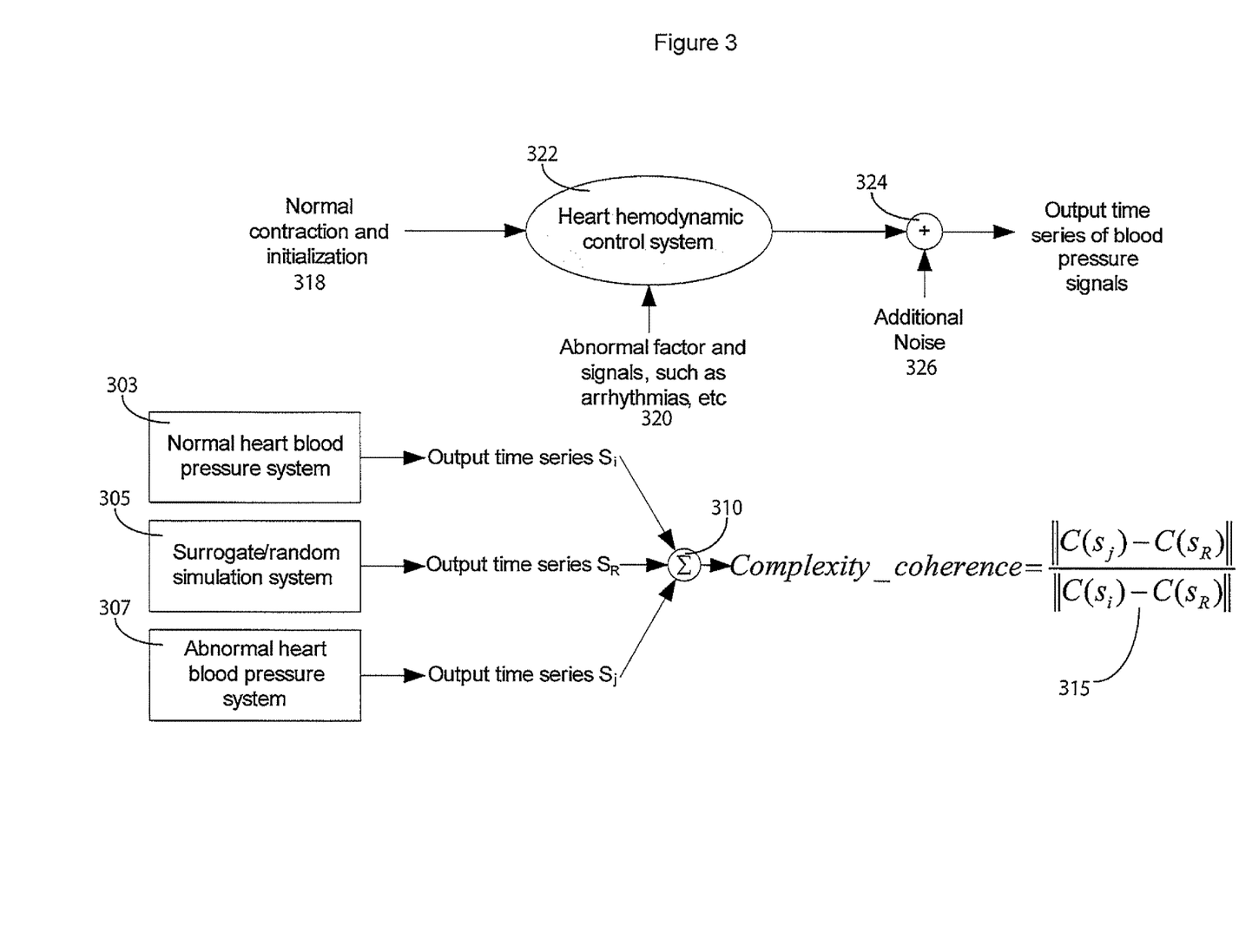
FIG. 3 shows a model and associated calculation for complexity coherence determination of a blood pressure signal, according to invention principles.

FIG. 3 shows a model and associated calculation for complexity coherence determination of a blood pressure signal performed by complexity processor 19. Specifically, system 10 in step 322 processes waveform data representing normal heart contraction and initialization 318 as well as waveform data representing abnormal factors such as arrhythmias 320 and additional noise 326, to provide a blood pressure data sample sequence. In one embodiment, complexity coherence is determined by calculating and comparing a complexity value for different parts of a hemodynamic signal, specifically a baseline episode and a current ongoing real time episode for the blood pressure data sample sequence. Processor 19 calculates a complexity coherence value 315 using a complexity value determined for a data sample series Si for normal blood pressure waveform data 303, a complexity value determined for a data sample series Sr for a random blood pressure waveform data 305 and a complexity value determined for a data sample series Sj for potentially abnormal blood pressure waveform data 307. Processor 19 calculates complexity coherence value 315 to capture nonlinear changes of a current ongoing pressure waveform. In complexity coherence calculation 315, the blood pressure digital data stream time series Sr Si Sj are synchronized and use a time window having a starting edge comprising a peak (Maximum) of one of the waveforms or use a time stamp (such as a stamp indicating EoS (End Systolic) point, EoD (End of Diastolic) point or a Minimum value, for example.

System 10 applies complexity theory to identify waveform data having the highest complexity. In normal operation, a normal heart contracts and squeezes and operates in an orderly manner and linearly with normal heart control rate. In response to an abnormal event, such as a cardiac pathology event or drug delivery, the normal working harmonics of the hemodynamic sequence may change and vary. Hemodynamic waveform signal data may be characterized as having a linear portion and a nonlinear portion. The nonlinear portion in a cardiac signal may increase due to severity of the cardiac function abnormality. When cardiac rhythm falls into arrhythmia (e.g. because of a clinical event), the nonlinear part increases which is identified by the system as a potential abnormal cardiac change. The nonlinearity changes in a blood pressure waveform are advantageously characterized by complexity coherence as:

$$\text{Complexity\_coherence} = \frac{\|C(s_j) - C(s_R)\|}{\|C(s_i) - C(s_R)\|}. \quad \text{equation 1}$$

In which, $S_i$, $S_j$ and $S_R$ are complexity calculation indexes for different time series, normal (baseline signals), ongoing real time signals, and random signals. $S_R$ typically does not change for a particular portion and length of a blood pressure waveform time data series, but is adjustable by change of a complexity coherence calculation window portion of the pressure waveform. The coherence calculation time window may be changed from one heart beat to multiple heart beats, for example, and a beat is identified using an ECG signal.

A beat for a blood pressure signal is indicated by Peak to Peak pressure, EoS (End-of-Systolic) to EoS, Minimum to minimum pressure, for example. $C(s_j)$–$C(s_R)$ represents the complexity distance (nonlinearity) from a current blood pressure waveform to a random waveform (e.g., random waveform data derived by a computer). $C(s_i)$–$C(s_R)$ represents a complexity distance from a normal (baseline) pressure waveform of the patient concerned to the random waveform. The nonlinearity calculation identifies a difference between a periodic blood pressure rhythm and random pressure waveform. Random signals are used as a maximum complexity to measure changes and distortions of blood pressure waveforms. Coherence (correlation) between different cardiac signals is determined by processor 19 (FIG. 1) by a variety of different equations in different formats. System 10 uses the coherence (or correlation) to calculate and quantify nonlinear changes, mode and pattern alternations and distortions in hemodynamic signals due to pathologies or clinical events.

Complexity coherence captures changes in hemodynamic signals in the time domain, such as a fast rhythm or low perfusion. However, substantial information is also available in the frequency domain in data representing frequency component changes in different bandwidths, for example.

System 10 uses multi-bandwidth spectrum coherence for interpretation of hemodynamic pressure waveforms and signals. Individual hemodynamic waveforms are reconstructed using sinusoidal waveforms which divide a pressure waveform signal into a linear correlated portion and a nonlinear (uncorrelated) portion. System 10 determines spectrum coherence changes occurring due to clinical events and cardiac function pathologies by analyzing the changes in particular blood pressure waveform portions.

A system 10 mathematical model of spectrum coherence, in one embodiment, processes blood pressure waveform data with P constituent sine waves (P is determined and adjusted by the system or user) that are taken at a given point of a signal x for example, including a random phase sinusoid comprising white noise so, $$x(t) = \sum_{i=1}^{P} (A_i \cos(\omega_i t + \theta_i) + B_i \cos(\omega_i t + \varphi_i)) + w(t)$$

where w(t) is the white noise, $A_i$ are amplitude terms and control gain of correlated sinusoids and $B_i$ are amplitude terms and control gain of uncorrelated sinusoids and $\theta_i$, and $\varphi_i$, are random phases. This applies to each sinusoid, i, such that $1 \leq i \leq P$ where P is the number of sinusoids. (In general, the number of correlated and uncorrelated sinusoids need not be equal.) At this point the spectrum coherence model at a given sinusoidal frequency is:

$$\gamma(\omega_i) = \frac{A_i^2}{A_i^2 + B_i^2}$$

A coherence function comprises a ratio of correlated to total (uncorrelated+correlated) power. The correlated power amplitudes can be written as:

$$\gamma_{xx}(f) = \frac{\frac{1}{N}\left|\sum_{n=1}^{N} X_n(f)\right|^2}{\frac{1}{N}\sum_{n=1}^{N} |X_n(f)|^2}$$

where $X_n(f)$ is the Fourier transform of the time series x(t).

Complexity coherence is calculated by combining the complexity computations of three series: baseline pressure signal series, on-going pressure signal series, and random data series. A baseline pressure signal is a normal signal from the patient (for example, acquired at the beginning of a case, a previous recording of data or comparable pressure data). Random data series are created using a computer which is used for maximum complexity comparison (Random signals have the biggest complexity calculation value and this increases with the length of the data series). For example, a 100 data sample (calculation window) is utilized for complexity coherence calculation. The complexity value of normal baseline pressure signals is 15 (typically 10-20) while for a random signal data series is 100. If the complexity of the real time on-going pressure data is 16 and is comparable with the baseline signal, it means the real time signal is normal and complexity coherence is 0.99 (near One) While, if the complexity calculation of the pressure signal is higher, for example 65, such as in arrhythmia or clinical event cases, the complexity coherence is 0.41. The smaller the value of complexity coherence, the more severe is arrhythmia.

System 10 calculates spectrum coherence in a similar manner to complexity coherence. For example, an on going real time data window is 100 points, $x_1, \ldots, x_N$. The spectrum is calculated for this 100 point $(X_1, \ldots, X_N)$ data series using a Fourier transform and the following is calculated, $$\gamma_{xx}(f) = \frac{\frac{1}{N}\left|\sum_{n=1}^{N} X_n(f)\right|^2}{\frac{1}{N}\sum_{n=1}^{N} |X_n(f)|^2} \qquad \text{equation 2}$$

In one embodiment system 10 uses equation 2 to derive a correlation power amplitude parameter value. The normal range of spectrum coherence values is from 0 to 1 and for a continuous real time normal and healthy blood pressure waveform, the spectrum coherence value is 1 and in the case of arrhythmia or clinical events such as myocardial ischemia or AF, the value is less than 1, for example.

System 10 derives a single measure comprising a spectrum coherence index indicating signal change using data representing a substantial portion of an entire signal spectrum. The spectrum coherence index measure indicates changes in spectra of a signal and indicates how distinct the changes are from a baseline template signal in various frequency bands. The frequency bandwidth templates signals are controlled and adjusted in response to clinical application and some frequency bands are not used to avoid noise effects.

$$\text{spectrum\_coherence} = \frac{\bar{\gamma}}{\bar{\gamma} + \sum_{\Omega} \Theta(|\hat{\gamma}(e^{j w}) - \bar{\gamma}|)} \qquad \text{equation 3}$$

with $$\Theta(x) = \begin{cases} 0.0, & \text{if } x < \Theta\bar{\gamma} \\ x, & \text{if } x \geq \Theta\bar{\gamma} \end{cases}.$$

where $0<\Theta<1$. Thus, the Spectrum coherence index is near 1 when the ongoing blood pressure waveform signal is healthy and spectrum coherence index of the blood pressure waveform decreases due to clinical events and pathologies.

The coherence analysis in one embodiment is used for analyzing a single channel blood pressure signal using a baseline beat waveform (or benign) signal. The coherence analysis in another embodiment is used for analyzing multi-channel signals provided by using different blood pressures obtained at different cardiac sites, for example, for comparison and correlation to identify relative changes and variation between heart chambers and input and output characteristics. System 10 processes multi-channel channel hemodynamic signals (invasive and non-invasive blood pressure signals) to derive a function mapping indicating a heart or whole circulation system function. In the spectrum coherence calculation a blood pressure digital data stream time series is synchronized for a spectrum coherence calculation. The synchronization uses a time window having a starting edge comprising a peak (Maximum) of one of the waveforms or uses a time stamp (such as a stamp indicating EoS (End Systolic) point, EoD (End of Diastolic) point or a Minimum value, for example.

Figure 4:
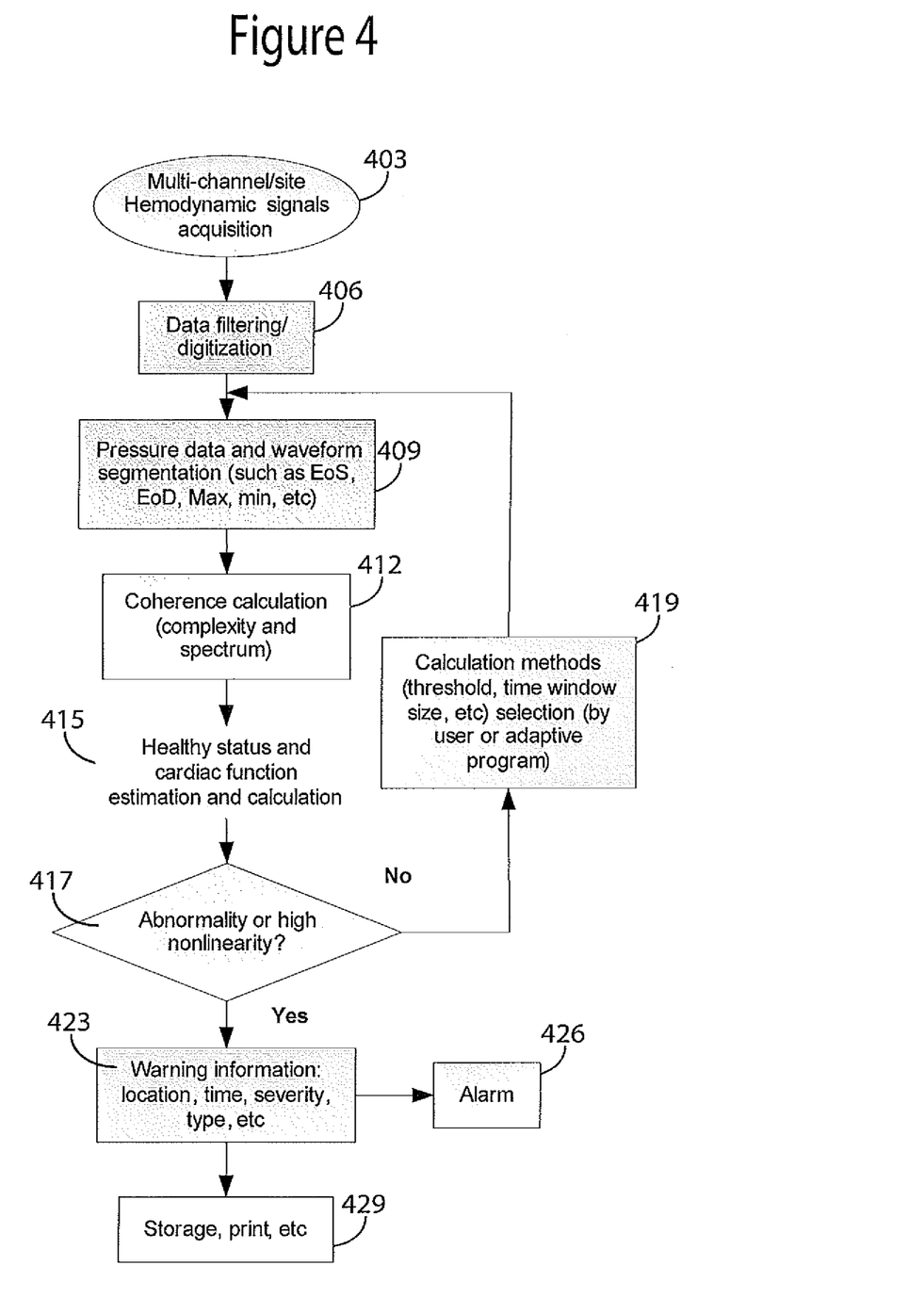
FIG. 4 shows a flowchart of a process for blood pressure waveform signal based coherence detection and interpretation, according to invention principles.

FIG. 4 shows a flowchart of a process for blood pressure waveform signal based coherence detection and interpretation performed by system 10 (FIG. 1). System 10 determines signal coherence for different channel blood pressure signals and identifies location, timing, severity and type of cardiac pathologies and diseases. System 10 quantifies a pattern of nonlinear changes occurring due to cardiac function variation and pathologies. Interface 12 in step 403 acquires blood pressure signals from multiple sensor channels and anatomical sites including different cardiac chambers. Interface 12 in step 406 digitizes and filters the acquired blood pressure signals using a filter adaptively selected in response to data indicating clinical application (e.g. ischemia detection, rhythm analysis application). In step 409 complexity processor 19 identifies different segments of blood pressure signal data (including peak, EoS, EoD sections, for example) of the filtered digitized blood pressure signals and data processor 20 initializes calculation parameters such as time window size, time step, symbolization level and warning threshold value.

In step 412, complexity processor 19 calculates a complexity coherence value, spectrum coherence value and spectrum coherence index value for the filtered, digitized blood pressure signals. Complexity processor 19 calculates first, second and third complexity indices for the corresponding first, second and third digital data sequences respectively. Correlation processor 15 uses the calculated first, second and third complexity indices to calculate one or more measures indicating deviation of the filtered, digitized blood pressure signals. In step 415 data processor 20 monitors the first, second and third complexity indices or values derived from these indices. Processor 20 determines abnormality and relatively high nonlinearity and generates an alert message in response to indices and values derived from these indices or a variation in the indices and values derived from these indices exceeding predetermined thresholds. Data processor 20 uses predetermined mapping information in repository 17, associating ranges of the indices or values derived from these indices with corresponding medical conditions, in comparing the indices or values derived from these indices with the ranges and generates an alert message indicating a potential medical condition.

If data processor 20 in step 415 identifies an abnormality or relatively high nonlinearity and associated medical condition indicating cardiac impairment or another abnormality, processor 20 in step 423 identifies the location, timing, severity and type of cardiac pathology and associated disease based on the anatomical location at which the blood pressure waveform is acquired. Processor 20 in step 423 also generates an alert message identifying the medical condition and abnormality and communicates the message to a user in step 426 and stores or prints the message and records the identified condition in step 429. If data processor 20 in step 417 fails to identify an abnormality or relatively high nonlinearity, in step 419 data processor 20 adaptively alters one or more calculation parameters such as time window size, time step, symbolization level and warning threshold value to improve abnormality detection.

Figure 5:
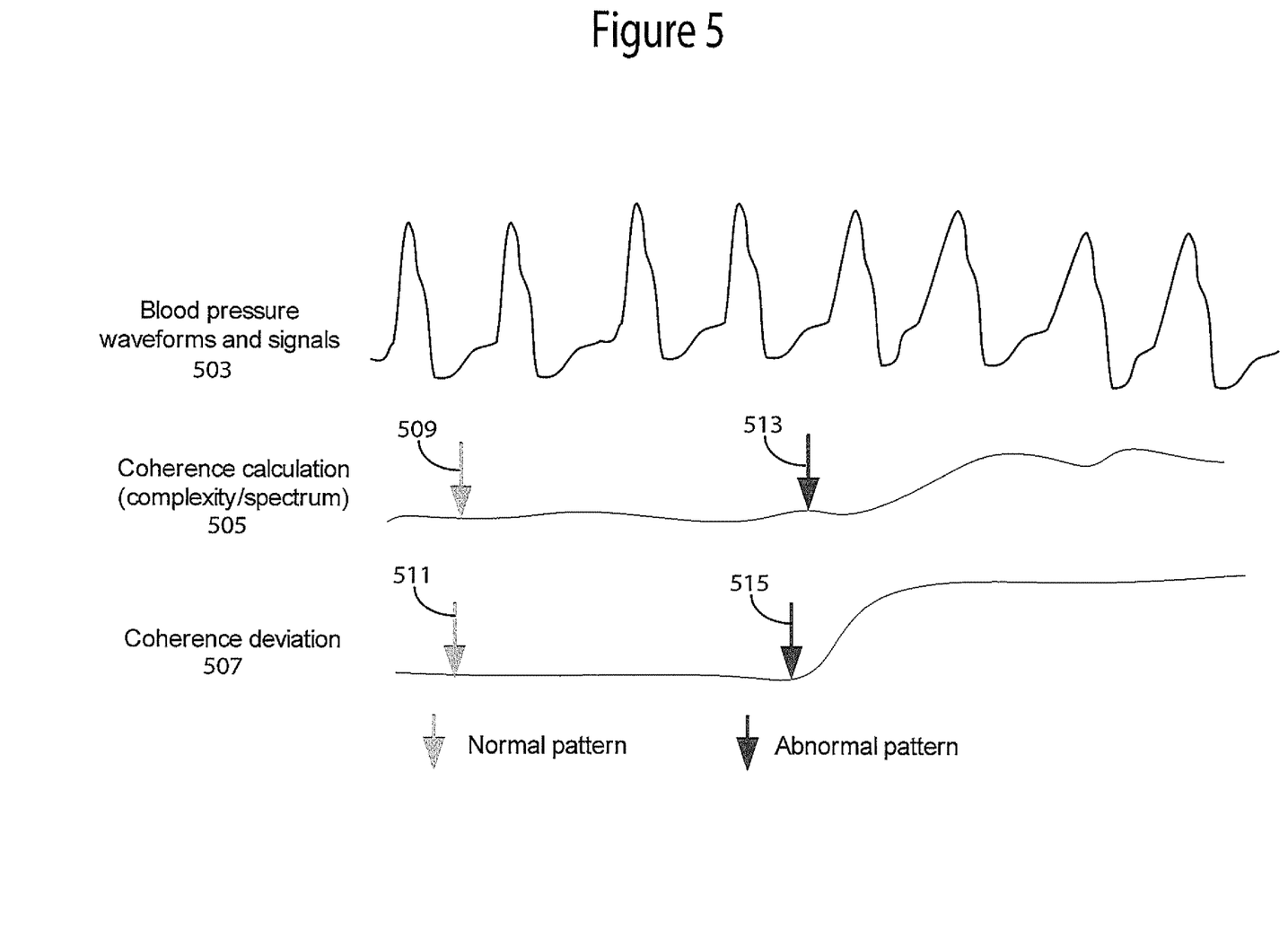
FIG. 5 shows hemodynamic pressure monitoring and interpretation based on coherence calculation, according to invention principles.

FIG. 5 shows hemodynamic pressure monitoring and interpretation based on coherence calculation. System 10 calculates and plots complexity coherence 505 and complexity coherence deviation 507 for blood pressure waveform 503. Data processor 20 monitors calculated data 505 and 507 and identifies normal points 509 and 511 as well as potentially abnormal points 513 and 515. The complexity coherence values identify events 513 and 515 and associated times which may potentially provide pathology detection and medical condition identification. Processor 20 further performs statistical analysis, including deviation, standard deviation and a hypothesis test on the calculated data 505 and 507 to improve detection of medical conditions.

System 10 (FIG. 1) analyzes blood pressure signal waveforms to identify and characterize small changes in heart tissue and cardiac functions. For example, due to certain diseases, one heart chamber (such as a left ventricle) may not work at normal squeezing speed, which may change a diastolic time period (including time length, pressure amplitude, period from EoS time to Maximum pressure time and rate of pressure change dP/dt). System 10 qualitatively and quantitatively captures and evaluates blood pressure waveform changes and identifies morphology patterns for different heart operation modes. Thereby system 10 provides early detection of negative changes in heart condition and functions and predicts future patient (cardiac function and circulation system) status and drug delivery indications. System 10 also employs combinations of different kinds of methods for blood pressure analysis including, cardiac stroke volume analysis, complexity calculation, time and amplitude ratio determination, complexity coherence calculation, spectrum and coherence calculation to improve hemodynamic pressure pattern interpretation. The pressure waveform analysis involves analysis of individual heart cycles and also averaging of data derived in a synchronized manner over multiple heart cycles (for example data averaging for the same heart cycle portion in different cycles) which improves signal to noise ratio.

Figure 6:
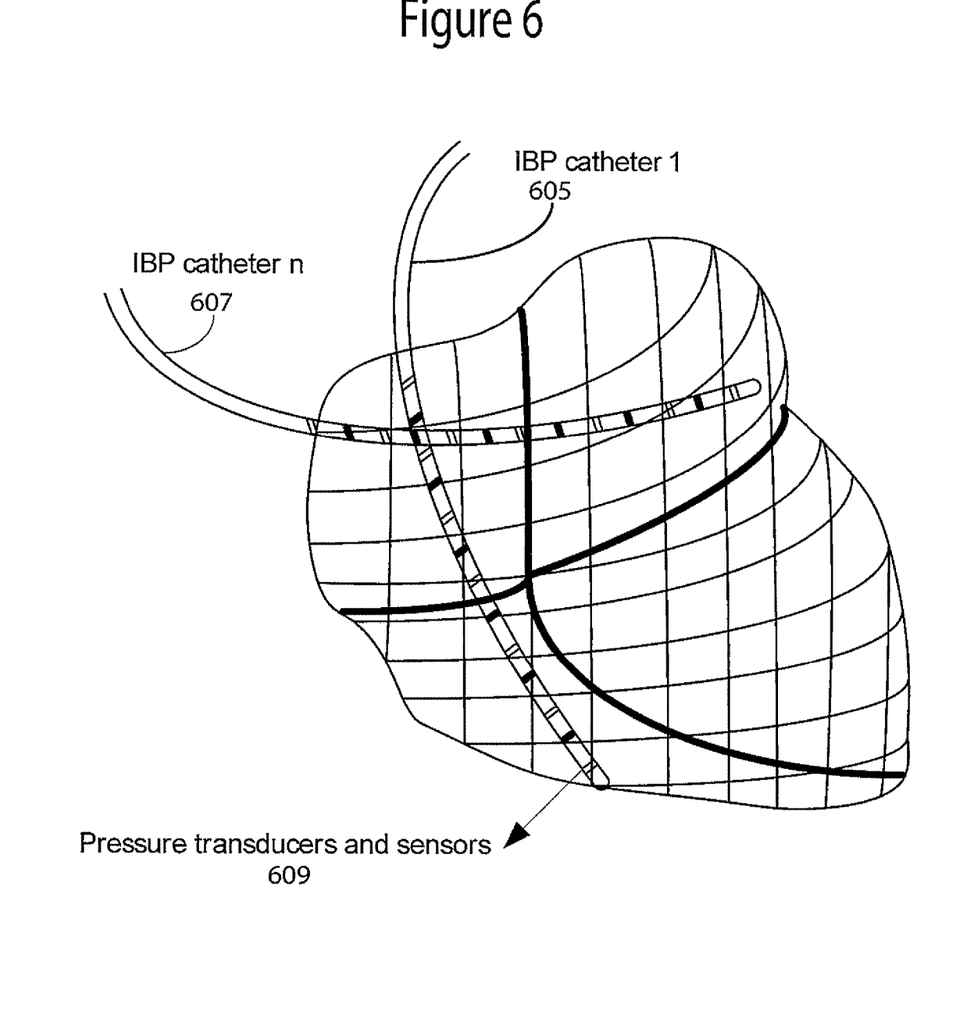
FIG. 6 shows multiple channel pressure signal coherence analysis and monitoring for cardiac event and pathology diagnosis, according to invention principles.

FIG. 6 shows multiple channel pressure signal coherence analysis and monitoring for cardiac event and pathology diagnosis. FIG. 6 shows an example of IBP (invasive blood pressure) catheters 605 and 607 used for hemodynamic pressure monitoring and analysis for atrium and ventricle chambers in a heart. The catheters include multiple blood pressure transducers and sensors 609 providing multiple pressure waveforms that are used for complexity coherence calculation by processor 19. Data processor 20 also performs coherence value pattern analysis using complexity coherence values calculated for pressure waveform data acquired at multiple different cardiac sites by catheters 605 and 607. Data processor 20 similarly determines and records data indicating different tissue working modes, such as of the left atrium, right atrium, and ventricles for comparison with data derived from the patient on a previous occasion or with data derived from a population of patients sharing demographic characteristics with the patient (e.g., age, weight, height, gender, pregnancy status). Data processor 20 uses predetermined mapping information in repository 17, associating ranges of complexity coherence values or values derived from complexity values with corresponding medical conditions, in comparing calculated complexity related values for the multiple cardiac pressure waveforms acquired by catheters 605 and 607 with the ranges and generates an alert message indicating a potential medical condition. Data processor 20 performs this complexity related data mapping for heart (internal) and whole circulation system (external) analysis.

Figure 8:
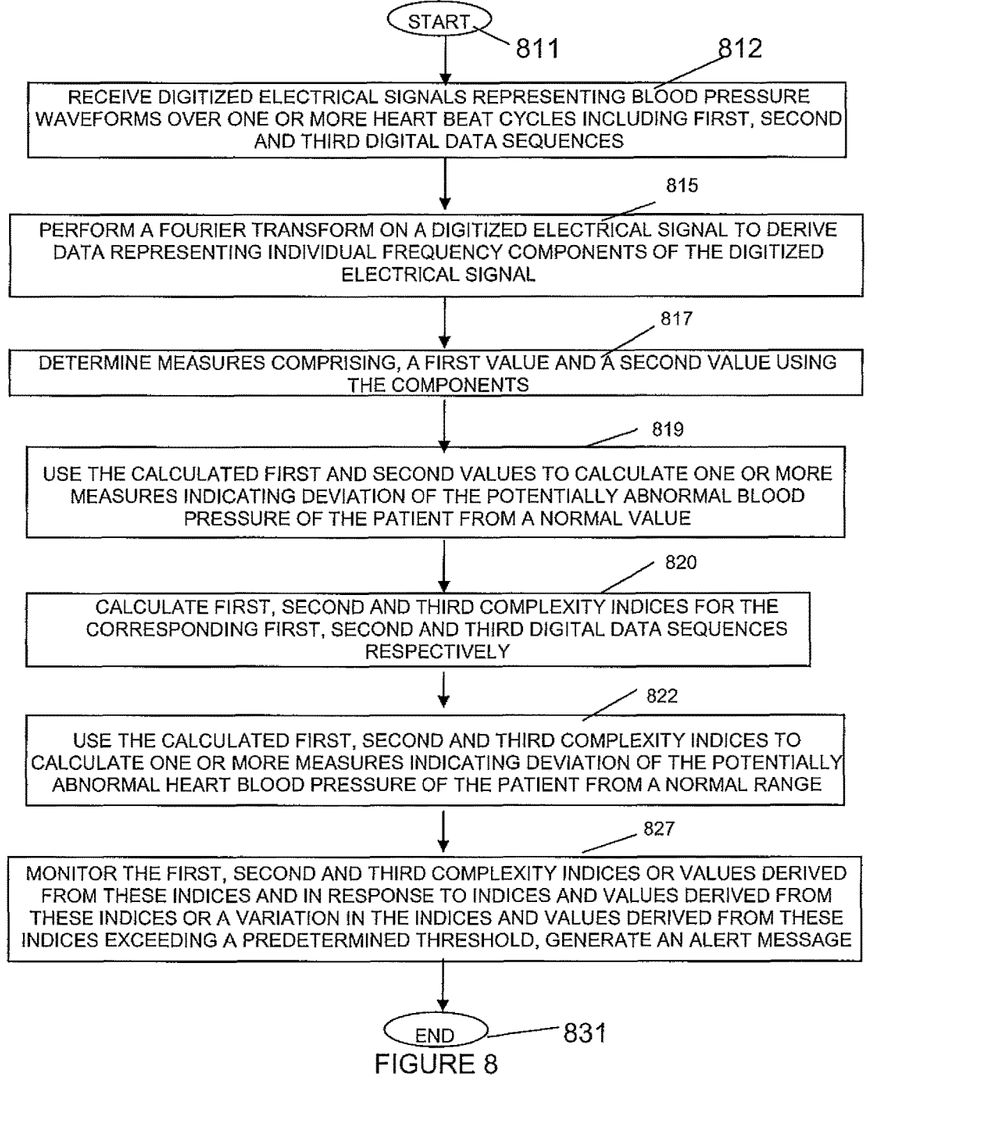
FIG. 8 shows a flowchart of a process used by a system for heart performance characterization and abnormality detection, according to invention principles.

FIG. 8 shows a flowchart of a process used by system 10 for heart performance characterization and abnormality detection. In step 812 following the start at step 811, interface 12 receives digitized electrical signals indicating first, second and third digital data sequences representing blood pressure waveforms over one or more heart beat cycles. Interface 12 substantially synchronizes the first, second and third digital data sequences in response to a peak or minimum value in the corresponding blood pressure waveforms. Interface 12 also substantially synchronizes a digitized electrical signal in response to a peak or minimum value in the corresponding blood pressure waveforms. The received signals comprise a first digital data sequence representing normal heart blood pressure of a patient, a second digital data sequence representing random heart blood pressure of a normal patient and a third digital data sequence representing a potentially abnormal heart blood pressure of a patient. In one embodiment, the first, second and third complexity indices comprise $S_i$, $S_R$ and $S_j$ respectively and the correlation processor calculates at least one of, (a) $C(s_j)-C(s_R)$ representing the complexity distance (nonlinearity) from a current blood pressure waveform to a random waveform and (b) $C(s_i)-C(s_R)$ representing a complexity distance from a normal (baseline) pressure waveform to a random waveform. Correlation processor 15 calculates ratio of (a) and (b). The first digital data sequence representing normal blood pressure of a patient is provided from stored blood pressure data of at least one of (i) the patient and (ii) a patient having similar demographic characteristics as the patient including at least one of age weight, gender and height and similar medical conditions as the patient.

In step 815, data processor 20 performs a Fourier transform on a digitized electrical signal to derive data representing individual frequency components of the digitized electrical signal. Calculation processor 24 in step 817 determines measures comprising first and second values. The first value represents a summation of the square of individual Fourier transform values of corresponding individual components of the individual frequency components. The second value represents a square of the summation of individual Fourier transform values of corresponding individual components of the individual frequency components. In step 819 correlation processor 15 uses the calculated first and second values to calculate one or more measures indicating deviation of the potentially abnormal blood pressure of the patient from a normal value.

In step 820 complexity processor 19 calculates first, second and third complexity indices for the corresponding first, second and third digital data sequences respectively. Correlation processor 15 in step 822 uses the calculated first, second and third complexity indices to calculate one or more measures indicating deviation of the potentially abnormal heart blood pressure of the patient from a normal range. Correlation processor 15 also calculates ratios (e.g., using equations 2 and 3) employing the first and second values in deriving a measure indicating deviation of the potentially abnormal blood pressure of the patient from a normal value.

Data processor 20 in step 827 monitors the first, second and third complexity indices or values derived from these indices and in response to indices and values derived from these indices or a variation in the indices and values derived from these indices exceeding a predetermined threshold, generates an alert message. Data processor 20 substantially continuously performs the monitoring for at least a 24 hour period. Further, data processor 20 uses predetermined mapping information, associating ranges of the indices or values derived from these indices with corresponding medical conditions, in comparing the indices or values derived from these indices with the ranges and generates an alert message indicating a potential medical condition. The predetermined mapping information associates ranges of the indices or values derived from these indices with particular patient demographic characteristics and with corresponding medical conditions and the data processor uses patient demographic data including at least one of, age weight, gender and height in comparing the indices or values derived from these indices with the ranges and generating an alert message indicating a potential medical condition. The process of FIG. 8 terminates at step 831.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a controller or microprocessor, for example, and is conditioned using executable instructions to perform special purpose functions not performed by a general purpose computer. A processor may be coupled (electrically and/or as comprising executable components) with any other processor enabling interaction and/or communication there-between. A user interface processor or generator is a known element comprising electronic circuitry or software or a combination of both for generating display images or portions thereof. A user interface comprises one or more display images enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a user interface processor and enabling user interaction with a processor or other device and associated data acquisition and processing functions.

The UI also includes an executable procedure or executable application. The executable procedure or executable application conditions the user interface processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

The system and processes of FIGS. 1-6 and 8 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The system performs blood pressure derived complexity data mapping for invasive and non-invasive blood pressure waveform data at multiple anatomical sites to identify medical conditions for different kinds of clinical application events. Further, the processes and applications may, in alternative embodiments, be located on one or more (e.g., distributed) processing devices on a network linking the units of FIG. 1. Any of the functions and steps provided in FIGS. 1-6 and 8 may be implemented in hardware, software or a combination of both.

APPENDIX

Symbolic Dynamics and Complexity Calculation

Figure 7:
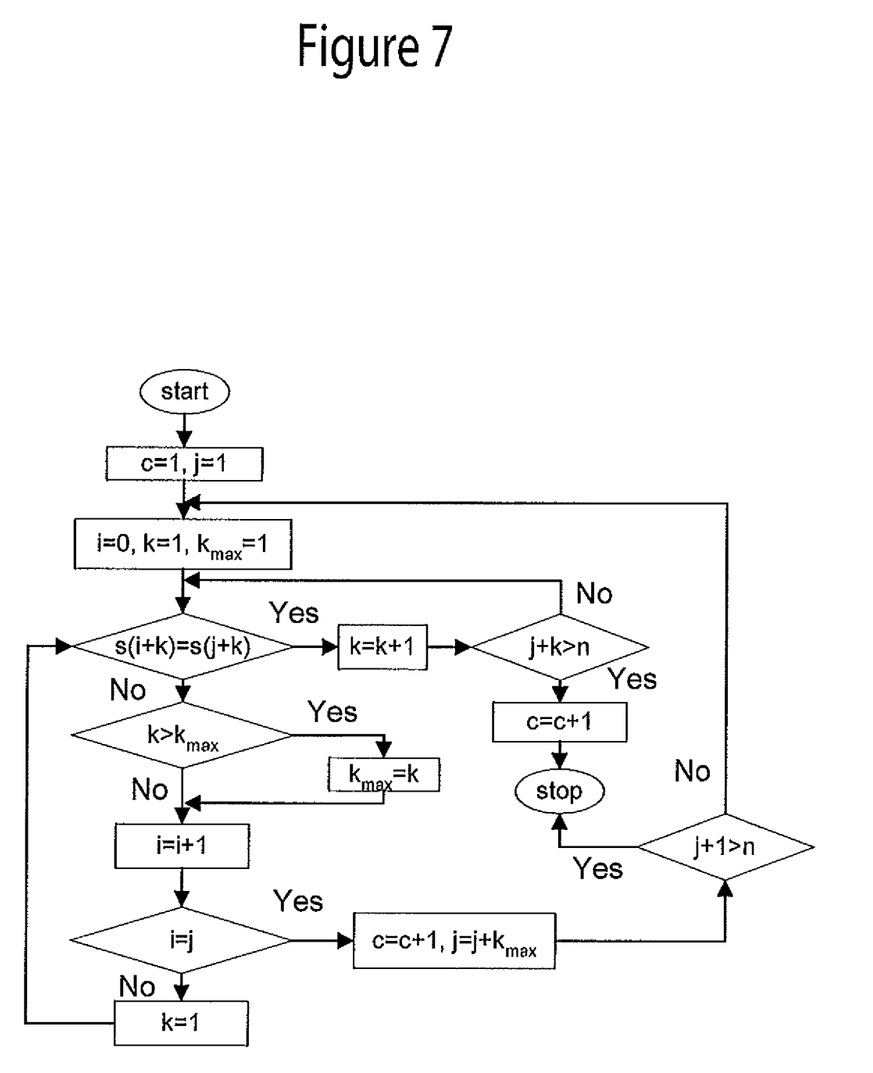
FIG. 7 shows a flowchart of a process for complexity calculation of symbolic strings $S = s_1 s_2 \ldots s$.

For simplicity, an embodiment considers 0-1 strings $s_1 s_2 \ldots s_n$ ($s_i$ is character 0 or 1, i=1, 2, ..., n). Let S, Q denote, respectively, two strings, and SQ be the concatenation of S and Q, while string SQ$\pi$ is derived from SQ after its last character is deleted ($\pi$ means the operation to delete the last character). Let v(SQ$\pi$) denote the vocabulary of all different substrings of SQ$\pi$. At the beginning, c(n)=1, S=$s_1$, Q=$s_2$, therefore, SQ$\pi$=$s_1$. For generalization, now suppose S=$s_1 s_2 \ldots s_r$, Q=$s_{r+1}$; if Q$\in$v(SQ$\pi$), then $s_{r+1}$ is a substring of $s_1 s_2 \ldots s_r$, therefore S doesn't change, and renew Q to be $s_{r+1} s_{r+2}$, then judge if Q belongs to v(SQ$\pi$) or not; and doing so in this way until Q$\notin$v(SQ$\pi$), now suppose Q=$s_{r+1} s_{r+2} \ldots s_{r+i}$, which is not a substring of $s_1 s_2 \ldots s_r s_{r+1} \ldots s_{r+i+1}$, thus increase c(n) by one. Thereafter combine S with Q and S is renewed to be S=$s_1 s_2 \ldots s_r s_{r+1} \ldots s_{r+i}$, while take Q as Q=$s_{r+i+1}$. Repeat above procedures until Q is the last character, at this time the number of different substrings of $s_1 s_2 \ldots s_n$ is c(n), i.e., the measure of complexity. Using two simple operations of comparison and accumulation, the computation of c(n) is implemented. FIG. 7 shows a flowchart of a process for complexity calculation of symbolic strings S=$s_1 s_2 \ldots s$.

Complexity Information Theory

The information extracted from the coarse-grain symbol dynamic sequences is limited, and speed information is not obtained by just complexity measurements. In abnormal cardiac signal analysis, a clinician desires to obtain accurate pathological information, such as for body fluid and nerve control interdiction, as well as of abnormal cardiac impedance signal extraction. The extracted complexity rate information is used to construct a correct and reasonable relationship between pathology and diagnosis parameters. On the basis of established complexity measures and the complexity method of extracted system features, the system present a method for complexity study involving symbolic dynamic system complexity rate information. The underlying cause of non-stationary dynamic change is uncovered with the help of this method.

Given a dynamic system time sequence X={$x_1, x_2, \ldots, x_i, \ldots$}, there exists subsequence $L_i$, $L_i$={$x_1, x_2, \ldots, x_i$}, in which i=1, 2, ..., n;

Utilizing the Lempel-Ziv (L-Z) complexity, corresponding complexity is computed for each subsequence $L_i$; $L_i$ and corresponds to complexity $c_i$.

C.1. Definition (Finite Sequence Complexity)
Suppose sequence $X=\{x_1, x_2, \ldots, x_i, \ldots\}$, there exists subsequence $L_i$, $L_i=\{x_1, x_2, \ldots, x_i\}$, in which $i=1, 2, \ldots$ n; define $c_n=\{c_1, c_2, \ldots, c_n\}$ as the corresponding complexity measure sequence of the sequence $X_n$, in which $c_i$ is the sequence complexity of the $L_i$, $X_n$ is the finite time sequence of X.

C.2. Definition (Time Sequence Complexity Rate)
Given a finite time sequence $X=\{x_1, x_2, \ldots, x_i, \ldots\}$, the corresponding finite complexity sequence is $c=\{c_1, c_2, \ldots c_n\}$, define complexity as follows:

$$cc(n) = \frac{c_{n_i} - c_{n_j}}{n_i - n_j}$$

in which $n_i - n_j$ is at least larger than Takens' embedding dimension in order to avoid spurious computation. cc(n) reflects the speed of the complexity change of the finite time sequence.

According to this definition, the complexity rate of the whole time sequence X(n) can be calculated from slope rate of the sequence fitting polynomial:

$$cc[x(n)] = \text{DIFF}[x(n)]$$

Based on the definition above, it is deduced:
C.2.1 when the time sequence is an infinite subsequence of a stochastic procedure, the corresponding maximum complexity is infinite and the complexity rate is 1.
C.2.2 when the time sequence is a finite subsequence of a stochastic procedure, the corresponding maximum complexity is a finite value and the complexity rate is 1.
C.2.3 when the time sequence is a subsequence of a periodic procedure, the corresponding complexity of the infinite subsequence is equal to that of finite effective subsequence and is a finite value. (Here the finite effective subsequence means that the length of the time sequence is enough for the effective complexity computation). That is, given a periodic time sequence $X=\{x_1, x_2, \ldots, x_i, \ldots\}$, there exists a constant N, when $i>N$, such that:

$$cc(i)=c,$$

in which the constant c is a finite value.
(Note that: to achieve algorithm standard and ease of comparison, the computing complexity of the time sequence has been standardized.)
C.2.4 when the time sequence is the output of a deterministic chaotic system, the corresponding complexity of its subsequence increases with the time series length. And if the corresponding complexity rate is $cc(n)_{chaos}$, then the $cc(n)_{chaos}$ is less than 1. And $cc(n)_{chaos}$ increases with the number of chaotic system dimension.
C.2.5 given a discrete time series of an arbitrary continuous deterministic chaotic system or a random system and the corresponding symbolic series complexity rate is $cc_m$, the maximum complexity can be approximately computed as follows:

$$c_x = cc_m \cdot l(x)$$

in which the $c_x$ is the time sequence complexity and the l(x) is the length of the symbol series (here linear fitting is used).
C.3. Average Complexity
Given a limited dynamic time sequence $X=\{x_1, x_2, \ldots, x_n\}$, in which $n<\infty$; the corresponding complexity sequence is $c_x=\{c_1, c_2, \ldots, c_n\}$, Then:

$$\overline{c_x} = \lim_{n\to\infty} \frac{1}{N} \sum_{i=1}^{n} c_i$$

Suppose the original procedure is continuous, the corresponding average complexity:

$$\overline{c_x} = \frac{1}{T} \int_0^T cc_i dx$$

What is claimed is:
1. A system for heart performance characterization and abnormality detection included in a medical device, the system comprising:
an interface configured to receive, from a blood pressure sensor coupled to the interface, digitized electrical signals representing blood pressure waveforms over one or more heartbeat cycles comprising,
a first digital data sequence representing a baseline blood pressure waveform of at least one of a first patient and a second patient having common characteristics as the first patient including at least one of age, weight, gender, height, and medical conditions,
a second digital data sequence representing a random blood pressure waveform that is derived by a computer and
a third digital data sequence representing an ongoing blood pressure waveform of the first patient;
a complexity processor configured to calculate first, second and third complexity values for the corresponding first, second and third digital data sequences respectively;
a correlation processor configured to determine one or more measures based on nonlinear changes of the ongoing blood pressure waveform with respect to the baseline blood pressure waveform and based on the first, second and third complexity values;
a data processor configured to determine a first anatomical location of the first patient and a type of cardiac pathology and/or associated disease based on the one or more determined measures and a second anatomical location of the first patient at which the ongoing blood pressure waveform is acquired; and
a transmitter configured to transmit a message to a user indicating the determined type of cardiac pathology and/or associated disease of the first patient.
2. The system according to claim 1, wherein
said interface substantially synchronizes the first, second and third digital data sequences.
3. The system according to claim 2, wherein
said interface substantially synchronizes the first, second and third digital data sequences in response to a peak or minimum value in the corresponding blood pressure waveforms.
4. The system according to claim 1, wherein the data processor is further configured to monitor said first, second and third complexity values and in response to a variation in the values exceeding a predetermined threshold, generate an alert message.
5. The system according to claim 4, wherein
said data processor substantially continuously performs the monitoring for at least a 24 hour period.

6. The system according to claim 4, wherein
said data processor uses predetermined mapping information, associating ranges of said values with corresponding medical conditions, in comparing said values with said ranges and generates an alert message indicating a potential medical condition.

7. The system according to claim 6, wherein
said predetermined mapping information associates ranges of said values with particular demographic characteristics for a population of patients and with corresponding medical conditions and said data processor uses patient demographic data for the population of patients including at least one of age, weight, gender and height in comparing said values with said ranges and generating the alert message indicating a potential medical condition.

8. The system according to claim 6, wherein
said first digital data sequence representing said baseline blood pressure waveform is provided from stored blood pressure data of at least one of (a) said first patient and (b) said second patient having common demographic characteristics as said first patient including the at least one of age, weight, gender, height, and medical conditions as said first patient.

9. A method for heart performance characterization and abnormality detection performed by a medical device, the method performed using a computer system of the medical device including a processor and comprising the activities of:
receiving, by the processor from a blood pressure sensor, digitized electrical signals representing blood pressure waveforms over one or more heartbeat cycles comprising,
a first digital data sequence representing a baseline heart blood pressure waveform of at least one of a first patient and a second patient having common characteristics as the first patient including at least one of age, weight, gender, height, and medical conditions,
a second digital data sequence representing a random blood pressure waveform derived by a computer and
a third digital data sequence representing an ongoing heart blood pressure waveform of the second patient;
calculating, by the processor, first, second and third complexity values for the corresponding first, second and third digital data sequences respectively;
determining, by the processor, one or more measures based on nonlinear changes of the ongoing heart blood pressure waveform with respect to the baseline heart blood pressure waveform and based on the first, second and third complexity values,
determining, by the processor, a first anatomical location and a type of cardiac pathology and/or associated disease based on the one or more determined measures and a second anatomical location of the second patient at which the ongoing blood pressure waveform is acquired; and
transmitting a message to a user indicating the determined type of cardiac pathology and/or associated disease of the second patient.

10. A system for heart performance characterization and abnormality detection included in a medical device, the system comprising:
an interface configured to receive, from a blood pressure sensor coupled to the interface, a digitized electrical signal representing a blood pressure waveform over one or more heartbeat cycles;
a data processor configured to perform a Fourier transform on said digitized electrical signal to derive data representing individual frequency components of said digitized electrical signal;
a calculation processor configured to determine measures comprising,
(a) a first value representing a summation of the square of individual Fourier transform values of corresponding individual components of said individual frequency components and
(b) a second value representing a square of the summation of individual Fourier transform values of corresponding individual components of said individual frequency components; and
a correlation processor configured to use the calculated first and second values to calculate one or more measures based on nonlinear changes of a blood pressure of a patient from a baseline blood pressure value;
a processor configured to determine a first anatomical location and a type of cardiac pathology and/or associated disease based on the one or more calculated measures and a second anatomical location of the patient at which the blood pressure waveform is acquired; and
a transmitter configured to transmit a message to a user indicating the determined location and the determined type of cardiac pathology and/or associated disease of the patient, wherein
said correlation processor is further configured to calculate a ratio employing said first and second values using the following equation, $$\gamma_{xx}(f) = \frac{\frac{1}{N}\left|\sum_{n=1}^{N} X_n(f)\right|^2}{\frac{1}{N}\sum_{n=1}^{N} |X_n(f)|^2},$$

where $\gamma_{xx}$ is a coherence function ration, $X_n(f)$ is a Fourier transform of data points $x_1, \ldots x_N$, N is a number of the data points and f is a frequency.

11. The system according to claim 10, wherein
said interface synchronizes said digitized electrical signal.

12. The system according to claim 11, wherein
said interface substantially synchronizes said digitized electrical signal in response to a peak or minimum value in the corresponding blood pressure waveforms.

13. The system according to claim 10, wherein
said correlation processor calculates a ratio employing said first and second values comprising, $$\text{spectrum\_coherence} = \frac{\bar{\gamma}}{\bar{\gamma} + \sum_{\Omega} \Theta(|\hat{\gamma}(e^{jw}) - \bar{\gamma}|)}$$

with $$\Theta(x) = \begin{Bmatrix} 0.0, & \text{if } x < \Theta\bar{\gamma} \\ x, & \text{if } x \geq \Theta\bar{\gamma} \end{Bmatrix}$$

where, x is a data point value, $\bar{\gamma}$ is a mean coherence function ratio, $\hat{\gamma}$ is a current calculated coherence function ratio, $\omega$ is a phase, j is an imaginary unit, $\Omega$ is a frequency spectrum and $\Theta$ is a fixed threshold value, $0 < \Theta < 1$ and the Spectrum coherence index is near 1 when the ongoing blood pressure waveform signal is healthy and spectrum coherence index of the blood pressure waveform decreases towards zero due to abnormality in a blood pressure waveform.

* * * * *